United States Patent
Petersen et al.

(10) Patent No.: US 11,833,197 B2
(45) Date of Patent: Dec. 5, 2023

(54) IMMUNOTHERAPY OF LEISHMANIASIS

(71) Applicant: University of Iowa Research Foundation, Iowa City, IA (US)

(72) Inventors: Christine Petersen, Iowa City, IA (US); Angela Toepp, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 3 days.

(21) Appl. No.: 16/969,889

(22) PCT Filed: Feb. 13, 2019

(86) PCT No.: PCT/US2019/017872
§ 371 (c)(1),
(2) Date: Aug. 13, 2020

(87) PCT Pub. No.: WO2019/160971
PCT Pub. Date: Aug. 22, 2019

(65) Prior Publication Data
US 2021/0008186 A1    Jan. 14, 2021

Related U.S. Application Data

(60) Provisional application No. 62/630,053, filed on Feb. 13, 2018.

(51) Int. Cl.
*A61K 39/002* (2006.01)
*A61K 39/008* (2006.01)
*A61K 39/00* (2006.01)

(52) U.S. Cl.
CPC ........ *A61K 39/008* (2013.01); *A61K 2039/54* (2013.01); *A61K 2039/545* (2013.01); *A61K 2039/552* (2013.01); *A61K 2039/55577* (2013.01)

(58) Field of Classification Search
None
See application file for complete search history.

(56) References Cited

U.S. PATENT DOCUMENTS

| | | | | |
|---|---|---|---|---|
| 5,780,591 A | * | 7/1998 | Matlashewski | C07K 16/20 530/820 |
| 8,734,815 B2 | * | 5/2014 | Fernandes | A61P 31/12 424/269.1 |
| 8,968,749 B2 | * | 3/2015 | Fernandes | A61K 39/008 424/269.1 |
| 2004/0170636 A1 | * | 9/2004 | Matlashewski | A61K 39/39 424/184.1 |

OTHER PUBLICATIONS

Regina-Silva et al (Vaccine. 2016. 34: 2233-2239).*
Murray, Henry (J. Immunol. Apr. 15, 2005. 174(8): 4916-4923).*
Grimaldi et al (PLoS one. Sep. 27, 2017. 12 (9): pp. 1-18).*
Borja-Carbera (Vaccine. 2004. 22: 2234-2243).*
Roatt et al (Front.Immunol. 2017 (217): 1-14).*
Zutshi et al (Vaccines. 2019. vol. 7: 1-33).*
Toepp et al (Vaccine. 2018. 36. pp. 6433-6441).*
G.P. Borja-Cabrera et al., "Effective immunotherapy against canine visceral leishmaniasis with the FML-vaccine", Vaccine 22 (2004) 2234-2243.
F. Dantas-Torres, "Leishmune® vaccine: The newest tool for prevention and control of canine visceral leishmaniosis and its potential as a transmission-blocking vaccine", Veterinary Parasitology 141 (2006) 1-8.
Fernandes et al., "Comparison of two commercial vaccines against visceral eishmaniasis in dogs from endemic areas: IgG, and subclasses, arasitism, and parasite transmission by xenodiagnosis", VAccine 32 (2014) 1287-1295.
Saraiva et al., "The FML-vaccine (Leishmune®) against canine visceral leishmaniasis: A transmission blocking vaccine", Vaccine 24 (2006) 2423-2431.

* cited by examiner

*Primary Examiner* — Jennifer E Graser
(74) *Attorney, Agent, or Firm* — Wood, Phillips, Katz, Clark & Mortimer

(57) ABSTRACT

The present invention relates to methods and compositions for treating leishmaniasis in mammals. The invention more particularly relates to immunotherapeutic treatment of *Leishmania* in infected mammals, and is suitable for treating animals (e.g., dogs) and humans. The invention may be used alone or in combination with conventional chemotherapeutic agents.

12 Claims, 4 Drawing Sheets

Specification includes a Sequence Listing.

SEQUENCE LISTING

```
<160> NUMBER OF SEQ ID NOS: 10

<210> SEQ ID NO 1
<211> LENGTH: 6
<212> TYPE: PRT
<213> ORGANISM: Leishmania sp.

<400> SEQUENCE: 1

Gly Pro Leu Ser Val Gly
1               5

<210> SEQ ID NO 2
<211> LENGTH: 10
<212> TYPE: PRT
<213> ORGANISM: Leishmania sp.

<400> SEQUENCE: 2

Pro Leu Ser Val Gly Pro Gln Ser Val Gly
1               5                   10

<210> SEQ ID NO 3
<211> LENGTH: 119
<212> TYPE: PRT
<213> ORGANISM: Leishmania sp.

<400> SEQUENCE: 3

Met Lys Ile Arg Ser Val Arg Pro Leu Val Val Leu Val Cys Val
1               5                   10                  15

Ala Ala Val Leu Ala Leu Ser Ala Ser Ala Glu Pro His Lys Ala Ala
                20                  25                  30

Val Asp Ala Gly Pro Leu Ser Val Asp Val Gly Pro Leu Ser Val Asp
            35                  40                  45

Val Gly Pro Leu Ser Val Gly Pro Gln Ser Val Gly Pro Leu Ser Val
    50                  55                  60

Gly Pro Gln Ser Val Asp Pro Leu Ser Val Asp Val Gly Pro Leu Ser
65                  70                  75                  80

Val Gly Pro Gln Ser Val Gly Pro Leu Ser Val Asp Val Gly Pro Leu
                85                  90                  95

Ser Val Gly Pro Gln Ser Val Gly Pro Leu Ser Val Gly Leu Gln Ala
            100                 105                 110

Val Asp Val Ser Pro Val Ser
            115

<210> SEQ ID NO 4
<211> LENGTH: 102
<212> TYPE: PRT
<213> ORGANISM: Leishmania sp.

<400> SEQUENCE: 4

Met Lys Ile Arg Ser Val Arg Pro Leu Val Val Leu Leu Val Cys Val
1               5                   10                  15

Ala Ala Val Leu Ala Leu Ser Ala Ser Ala Glu Pro His Lys Ala Ala
                20                  25                  30

Val Asp Val Gly Pro Leu Ser Val Asp Val Gly Pro Leu Ser Val Asp
```

```
                35                  40                  45
Val Gly Pro Leu Ser Val Gly Pro Gln Ser Val Gly Pro Leu Ser Val
 50                  55                  60

Gly Pro Gln Ser Val Gly Pro Leu Ser Val Asp Val Gly Pro Leu Ser
 65                  70                  75                  80

Val Gly Pro Gln Ser Val Gly Pro Leu Ser Val Gly Pro Gln Ser Val
                 85                  90                  95

Asp Val Ser Pro Val Ala
            100

<210> SEQ ID NO 5
<211> LENGTH: 88
<212> TYPE: PRT
<213> ORGANISM: Leishmania sp.

<400> SEQUENCE: 5

Met Lys Ile Arg Ser Val Arg Pro Leu Val Val Leu Leu Val Cys Val
 1               5                  10                  15

Ala Ala Val Leu Ala Leu Ser Ala Ser Ala Glu Pro His Lys Ala Ala
                 20                  25                  30

Val Asp Val Gly Pro Leu Ser Val Asp Val Gly Pro Leu Ser Val Gly
             35                  40                  45

Pro Gln Ser Val Gly Pro Leu Ser Val Gly Pro Gln Ala Val Gly Pro
 50                  55                  60

Leu Ser Val Gly Pro Gln Ser Val Gly Pro Leu Ser Val Gly Leu Gln
 65                  70                  75                  80

Ala Val Asp Val Ser Pro Val Ser
                 85

<210> SEQ ID NO 6
<211> LENGTH: 113
<212> TYPE: PRT
<213> ORGANISM: Leishmania sp.

<400> SEQUENCE: 6

Met Lys Ile Arg Ser Val Arg Pro Leu Val Val Leu Leu Val Cys Val
 1               5                  10                  15

Ala Ala Val Leu Ala Leu Ser Ala Ser Ala Glu Pro His Lys Ala Ala
                 20                  25                  30

Val Asp Val Gly Pro Leu Ser Val Asp Val Gly Pro Leu Ser Val Gly
             35                  40                  45

Pro Gln Ser Val Gly Pro Leu Ser Val Gly Pro Leu Ser Val Gly Pro
 50                  55                  60

Gln Ala Val Gly Pro Leu Ser Val Gly Pro Gln Ala Val Gly Leu Leu
 65                  70                  75                  80

Ser Val Gly Pro Gln Ser Val Gly Pro Leu Ser Val Gly Pro Gln Ser
                 85                  90                  95

Val Gly Pro Leu Ser Val Gly Leu Gln Ala Val Asp Val Ser Pro Val
            100                 105                 110

Ser

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
aagtgctttc ccatcgcaac t                                               21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcactaaac ccctccaa                                                   18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cggttcggtg tgtggcgcc                                                  19

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5
```

IMMUNOTHERAPY OF LEISHMANIASIS

PRIORITY APPLICATION

This application is a U.S. National Phase of PCT Application No. PCT/US2019/017872 filed Feb. 13, 2019 which claims priority to U.S. Provisional Application No. 62/630,053 that was filed on Feb. 13, 2018. The entire contents of the application referenced above is hereby incorporated by reference herein.

BACKGROUND

Leishmaniasis covers a spectrum of mammalian diseases caused *Leishmania* protozoans. The disease ranges from asymptomatic to self-healing skin ulcers to fatal visceral infections. Visceral leishmaniasis (VL) is a severe and often lethal disease if not treated soon after onset of symptoms.

Leishmaniasis is mainly a canine zoonosis. The parasites are exposed on the skin of dogs, foxes, and wild dogs, and are often transmitted to humans via a transmission cycle involving insects called sandflies. Other routes of administration are possible (such as placental, blood wounds and fights). The *Leishmania* protozoans exist in two forms: the extracellular flagellated promastigotes, and the non-flagellated amastigotes. The amastigote form of the parasite is responsible for the pathology inside mammals. Flagellated promastigotes are present in the alimentary tract of the insects and can be transmitted to mammalian host through the bite of the insect vector. Once introduced, the promastigotes are taken up by macrophages where they differentiate into the amastigote form, which multiplies, causing destruction of the infected cells and leading to the various symptoms associated with leishmaniasis.

Several different species and subspecies of parasites of the genus *Leishmania* have been identified. Some of the most important species are *L. donovani*, *L. infantum*, *L. chagasi*, *L. braziliensis*, *L. tropica* and *L. major*, for instance. *L. donovani*, *L. chagasi* and *L. infantum* cause visceral leishmaniasis (also known as kala-azar), *L. brasiliensis* causes mucocutaneous leishmaniasis and *L. major* causes cutaneous leishmaniasis.

Diagnosis of leishmaniasis is complex, especially at early stages of the disease when the infected animal can be asymptomatic. Up to 25% of the dog population in a given endemic area can be infected and asymptomatic. In endemic areas, it can be difficult to differentiate animals that should be protected against a potential new infection from those, already infected, who should be treated. There is therefore a need for a preventive vaccine with a good tolerance and therapeutic effects.

Treatment of homes with insecticides, treatment of dogs with repellent insecticides and preventive vaccination of humans and dogs against visceral leishmaniasis are regarded as the best tools for control and eradication of the disease. Various types of vaccines against *Leishmania* have been proposed, including live parasites; frozen promastigotes from culture; sonicated promastigotes; gamma-irradiated live promastigotes; and formalin-killed promastigotes treated with glucan. Canine vaccines are available, including Leishmune®. They use as immunogen a purified parasite antigen. While such vaccines appear efficient, they cannot fully prevent infections of dogs or other mammals. Also, mammals are not all vaccinated, so that dogs still represent possible domestic leishmaniasis reservoirs. Also, pharmaceutical agents used to treat leishmaniasis, such as dehydroemetine or amphotericin B, exert, apart from the desired activity, very toxic and adverse side effects.

Furthermore, in some countries, like Brazil, wherein the disease is very common, it's illegal for veterinarians to treat dogs seropositive for canine leishmaniasis due to the risk of these animals failing treatment and promoting *Leishmania* transmission to people.

Accordingly, there is a need for further therapies of leishmaniasis in infected animals, particularly in dogs and humans.

SUMMARY

The present invention relates to methods and compositions for treating leishmaniasis in mammals. The invention more particularly relates to immunotherapeutic treatment of *Leishmania* in infected mammals, and is suitable for treating animals (e.g., dogs) and humans. The invention may be used alone or in combination with conventional chemotherapeutic agents.

The invention relates to methods for treating leishmaniasis in an infected mammal, comprising administering to the mammal a *Leishmania* A2 polypeptide.

A further object of the invention is a method for treating a *Leishmania* infection in an infected mammal, comprising administering to the mammal a *Leishmania* A2 polypeptide.

A further object of the invention is a method for delaying the appearance of leishmaniasis clinical signs and preventing the health status of the infected animal from worsening, comprising administering to the mammal a *Leishmania* A2 polypeptide.

A further object of the invention is a method for reducing leishmaniasis clinical signs in number and severity in an infected mammal, comprising administering to the mammal a *Leishmania* A2 polypeptide.

A further object of the invention is a method for preventing the spread of leishmaniasis from infected mammal, comprising administering to the mammal a *Leishmania* A2 polypeptide. Another object of the invention resides in a method for reducing *Leishmania* load in an infected mammal, comprising administering to the mammal a *Leishmania* A2 polypeptide.

The invention also relates to a method for clarifying or generating partial or total clearance of *Leishmania* in an infected mammal, comprising administering to the mammal a *Leishmania* A2 polypeptide.

The invention also relates to a *Leishmania* A2 polypeptide for use in treatment of leishmaniasis or of a *Leishmania* infection in an infected mammal.

The invention also relates to a *Leishmania* A2 polypeptide for use in reducing *Leishmania* load, or in delaying the appearance of Leishmaniasis clinical signs, or in reducing leishmaniasis clinical signs in number and severity, in an infected mammal.

The invention further relates to a *Leishmania* A2 polypeptide for use for preventing the spread of leishmaniasis from an infected mammal.

The invention also relates to a *Leishmania* A2 polypeptide for use for clarifying or generating partial or total clearance of *Leishmania* in an infected mammal.

The invention may be used in any mammal, such as humans and non-human mammals, particularly dogs or humans.

The A2 polypeptide may be formulated with any suitable excipient, and may optionally be used with an adjuvant. The immunotherapy of the invention may be used alone, or in combination with other treatment(s) such as chemotherapy.

The invention is suitable for treating any leishmaniasis, particularly visceral leishmaniasis (VL).

BRIEF DESCRIPTION OF THE FIGURES

FIG. 4A. Impact of vaccine/immunotherapy on ability to return to asymptomatic status. White bars—vaccinated dogs, black bars—dogs who received placebo. FIG. 4B. Progression or regression of disease in symptomatic animals over the course of the trial based on clinical score from month 9-clinical score at enrollment. White bars—vaccinated dogs, black bars-dogs who received placebo. FIG. 4C. Mortality in animals that became symptomatic during vaccination series. White bars—vaccinated dogs, black bars-dogs who received placebo. These changes were not significant due to a small n, total n=11 or 10.

DETAILED DESCRIPTION

Figure 1:
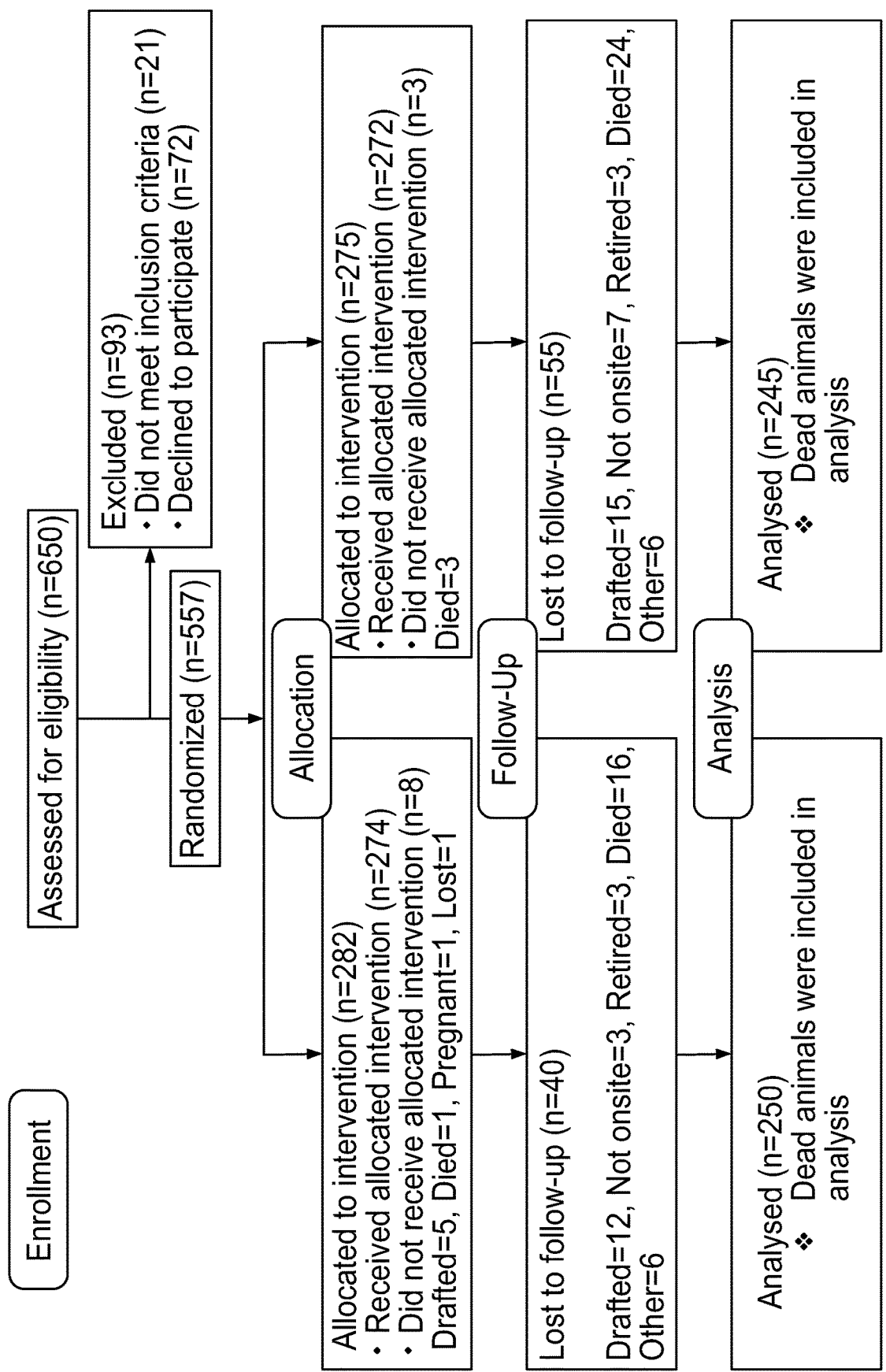
FIG. 1. CONSORT diagram for trial.

The invention provides novel immunotherapy methods for treating leishmaniasis in mammals.

Leishmaniasis

Leishmaniasis designates any disease or symptoms caused by *Leishmania* infection. Leishmaniasis can be classified as cutaneous, mucocutaneous, or visceral, in reference to their tissue tropism and the clinical causing symptoms.

The invention may be used to treat any *Leishmania*. It is particularly suited to treat visceral leishmaniasis or cutaneous leishmaniasis, more particularly visceral leishmaniasis. In this regard, in a particular embodiment, the invention relates to the treatment of canine or human visceral leishmaniasis.

Visceral leishmaniasis (VL) is mainly caused by *L. infantum* and *L. donovani*. Symptoms of the disease include intermittent fever, anemia, splenomegaly, hepatomegaly, and lymphadenopathy. The outcome of VL is often death.

In dogs, infected animals can be asymptomatic and the diagnosis can be difficult to determine. When the disease develops, the most common clinical symptoms of leishmaniasis are generalized lymphadenomegaly, lethargy, splenomegaly, polyuria, polydypsia, diarrhea, onychogryphosis, dermatitis with loss of hair, especially around the eyes, ears, and nose. In a more advanced stage of the disease, the dogs can lose weight and exhibit epistaxis, neurological signs, ocular signs, wounds in the skin, as well as symptoms related to kidney failure.

The term treatment designates, within the context of the invention, any amelioration of the status of the treated infected mammal. Treatment includes, for instance, suppression or reduction of a symptom, improved quality of life, a delay in the progression of the disease, suppression or reduction of parasitemia (e.g., parasite load), an increase of parasite clearance, or an increase of survival.

A2 Polypeptide

The invention provides a novel immunotherapeutic method for treating leishmaniasis based on the administration of a *Leishmania* A2 polypeptide. As shown in the examples, such administration, in infected mammals, reduces leishmaniasis symptoms and increases survival. The method may be used in any mammal, and is particularly suited for treating infected dogs.

The term "A2 polypeptide" designates any naturally-occurring A2 protein produced by a *Leishmania* parasite, as well as fragments and/or derivatives thereof.

*Leishmania* A2 protein is encoded by the A2 gene in *Leishmania* and has been sequenced from many different species and subspecies of parasites of the genus *Leishmania*. Such sequences are generally available in the literature, such as in Genbank (see e.g., accession numbers S69693; S69693.1; 546453; AAP21105.1, AAP21104.1, or APP21103.1, or ADT91620.1, for instance). A2 proteins have also been disclosed in several patents, such as U.S. Pat. No. 5,780,591, WO9506729, or EP0716697.

A2 proteins of *Leishmania* typically contain a sequence of a stretch of 6 amino acids, repeated several times (e.g., from 2 to 10) depending on the "A2 family" gene (Charest & Matlashewski. Mol. Cell. Biol.: 14, 1994; Zhang et al., Mol. Bioch. Parasitol.: 78, 1996), Preferably, the A2 polypeptide is an A2 protein of an amastigote form of *Leishmania*.

In another particular embodiment, the A2 polypeptide is an A2 protein from a *Leishmania* species selected from *L. donovani, L. infantum, L. chagasi, L. braziliensis, L. tropica* or *L. major*.

In a particular embodiment, the A2 polypeptide comprises the sequence GPLSVG (SEQ ID NO: 1), preferably several repeats of said sequence.

In a further particular embodiment, the A2 polypeptide comprises the sequence PLSVGPQSVG (SEQ ID NO: 2), preferably several repeats of said sequence.

Examples of native A2 proteins from different species of *Leishmania* are provided below:

```
                                          (SEQ ID NO: 3)
MKIRSVRPLVVLLVCVAAVLALSASAEPHKAAVDAGPLSVDVGPLSVDVG

PLSVGPQSVGPLSVGPQSVDPLSVDVGPLSVGPQSVGPLSVDVGPLSVGP

QSVGPLSVGLQAVDVSPVS (SEQ ID NO: 4)
MKIRSVRPLVVLLVCVAAVLALSASAEPHKAAVDVGPLSVDVGPLSVDVG

PLSVGPQSVGPLSVGPQSVGPLSVDVGPLSVGPQSVGPLSVGPQSVDVSP

VA (SEQ ID NO: 5)
MKIRSVRPLVVLLVCVAAVLALSASAEPHKAAVDVGPLSVDVGPLSVGPQ

SVGPLSVGPQAVGPLSVGPQSVGPLSVGLQAVDVSPVS (SEQ ID NO: 6)
MKIRSVRPLVVLLVCVAAVLALSASAEPHKAAVDVGPLSVDVGPLSVGPQ

SVGPLSVGPLSVGPQAVGPLSVGPQAVGLLSVGPQSVGPLSVGPQSVGPL

SVGLQAVDVSPVS
```

The A2 polypeptide may be a naturally-occurring *Leishmania* A2 protein, preferably in isolated or purified form.

The A2 polypeptide may be a derivative of a naturally-occurring *Leishmania* A2 protein, preferably in isolated or purified form. The term "derivative" designates preferably any polypeptide having one or several amino acid substitution, deletion or insertion as compared to the reference protein. Preferably, the derivative shall retain at least 85% amino acid sequence identity over the entire length of the protein, even more preferably at least 90%, at least 91%, at least 92%, at least 93%, at least 94%, at least 95%, at least 96%, at least 97%, at least 98%, at least 99%. The extent of sequence identity may be determined using any computer program and associated parameters, including BLAST 2.2.2 or FAS TA version 3.0t78, with the default parameters. Particular derivatives contain from 1 to 10 amino acid modifications as compared to the reference A2 protein. Furthermore, derivatives may contain non-natural amino acid residues, or protective groups, or other chemical functions that enhance their stability, immunogenicity, or purification, for instance. Examples of such additional function include a tag (such as a His tag) that facilitates purification.

Derivatives also include proteins with non-natural glycosylation, or devoid of glycosylation.

Further examples of derivatives include polypeptides conjugated to a carrier, or fusion proteins.

The A2 polypeptide may be, or may comprise or consist of, a fragment of a naturally-occurring *Leishmania* A2 protein or derivative, preferably in isolated or purified form. The term fragment designates preferably any portion of such a protein comprising at least 6, more preferably at least 10, even more preferably at least 15, at least 20, or at least 30 consecutive amino acids of said protein. Preferred fragments are immunogenic fragments, i.e., shall contain an epitope of A2 protein, or shall generate anti-A2 antibodies when administered to a mammal.

The A2 polypeptide may be produced by any method known per se in the art, such as artificial synthesis, enzymatic techniques, recombinant technology, or combinations thereof.

In a preferred embodiment, the A2 polypeptide is a recombinant polypeptide. Recombinant polypeptides may be produced from any host, such as prokaryotic (e.g., bacterium such as *E. coli*) or eukaryotic (e.g., plant, fungi, yeasts, mammalian) cells. recombinant production comprises introducing a coding nucleic acid sequence in the selected host under conditions allowing expression, and collecting the protein produced.

In a particular embodiment, the A2 polypeptide is a recombinant A2 polypeptide produced in prokaryotic cells, such as *E. coli*. For the production of the recombinant A2 protein or polypeptide in e.g., *E. coli*, the coding sequence of this polypeptide can be cloned in an expression vector, such as pET. A suitable bacterium, such as DL21 *E. coli* strain, is then transformed under conditions allowing expression of the A2 protein.

The protein may be purified using conventional techniques. Also, the protein may be prepared with a tag, such as a 6 His tag, which allows the purification of the recombinant protein through affinity chromatography for nickel.

Identity of the A2 protein sequence and structure prepared by recombinant technique can be verified e.g., by electrophoresis tests in SDS-PAGE systems, Western-Blot tests and/or DNA sequencing.

Nucleic Acids

The present invention provides nucleic acids that encode A2 polypeptides. The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

The terms "polynucleotide", "nucleic acid" and "nucleic acid fragment" are used interchangeably herein. These terms encompass nucleotides connected by phosphodiester linkages. A "polynucleotide" may be a ribonucleic acid (RNA) or deoxyribonucleic acid (DNA) polymer that is single- or double-stranded, that optionally contains synthetic, non-natural or altered nucleotide bases. A polynucleotide in the form of a polymer of DNA may comprise one or more segments of cDNA, genomic DNA, synthetic DNA, or mixtures thereof. Nucleotide bases are indicated herein by a single letter code: adenine (A), guanine (G), thymine (T), cytosine (C), inosine (I) and uracil (U). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleotide sequence" is a polymer of DNA or RNA that can be single-stranded or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

"Genome" refers to the complete genetic material of an organism.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods. Certain methods to determine identity are designed to give the largest match between the sequences tested. Methods to determine identity and similarity are codified in publicly available computer programs.

Nucleic acid molecules encoding amino acid sequence of A2 polypeptide are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the A2 polypeptide.

Promoters

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

In certain embodiments, the present invention provides vectors and expression cassettes containing the promoters described above. A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

Nucleic acids encoding therapeutic compositions can be engineered into a vector using standard ligation techniques. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration).

In certain embodiments, the present invention provides a vector containing an expression cassette comprising a promoter operably linked to a target sequence (e.g., A2 polypeptide) for production. "Expression cassette" as used herein means a nucleic acid sequence capable of directing expression of a particular nucleotide sequence in an appropriate host cell, which includes a promoter operably linked to the nucleotide sequence of interest that may be operably linked to termination signals. The coding region usually codes for a functional RNA of interest, for example an RNAi molecule. The expression cassette including the nucleotide sequence of interest may be chimeric.

"Operably-linked" refers to the association of nucleic acid or amino acid sequences on single molecular fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

"Expression" refers to the transcription and/or translation of an endogenous gene or a transgene in cells. For example, in the case of anti sense constructs, expression may refer to the transcription of the anti sense DNA only. In addition, expression refers to the transcription and stable accumulation of sense (mRNA) or functional RNA Expression may also refer to the production of protein.

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The coding region usually codes for a protein of interest but may also code for a functional RNA of interest, for example anti sense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Such expression cassettes will comprise the transcriptional initiation region linked to a nucleotide sequence of interest. Such an expression cassette may be provided with a plurality of restriction sites for insertion of the gene of interest to be under the transcriptional regulation of the regulatory regions. The expression cassette may additionally contain selectable marker genes.

The present disclosure also provides a mammalian cell containing a vector described herein.

Compositions

The A2 polypeptide of the invention may be used in isolated form. The term "isolated" is meant to refer to a protein which is in other than a native environment. For example, the protein may be a component of a cell culture or other artificial medium; a component of a pharmaceutical composition; or partially or completely purified from its native environment. The A2 polypeptide is preferably purified to at least 90% purity before being formulated and used in the invention.

The A2 polypeptide is preferably formulated with any suitable excipient or diluent. The compositions may also contain additional ingredients such as one or more adjuvant, preservative, antioxidant, etc.

Examples of pharmaceutically acceptable excipients or diluents include, but are not limited to demineralised or distilled water; saline solution; vegetable based oils such as peanut oil, arachid oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methyl cellulose, ethyl cellulose, carboxymethylcellulose, carboxymethylcellulose sodium salt, or hydroxypropyl methylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, I,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

The term "adjuvant" as used herein refers to non-specific stimulators of the immune response or substances that allow generation of a depot in the host, which when combined with the A2 polypeptide and pharmaceutical composition, respectively, of the present invention may provide for an even more enhanced immune response. The compositions commonly contain two components: antigen (e.g., A2 polypeptide) and adjuvant. The antigen is the molecular structure encoded by the pathogen or tumor against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered. Striking the right balance among these components is important to eliciting the desired immunological result. Examples of adjuvants include, but are not limited to, oil in water emulsions, aluminum hydroxide (alum), immunostimulating complexes, non-ionic block polymers or copolymers, cytokines (like IL-I, IL-2, IL-7, IFN-[alpha], IFN-[beta], IFN-y, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-a, 1β, 2, 4, 5, 6, 7, 8 and 10, 12, 13, 14, 15, 16, 17 and 18 (and its mutant forms); the interferons-a,β and y; granulocyte-macrophage colony stimulating factor (GM-CSF); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-I and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-I, and vascular endothelial growth factor; receptor molecules including Fas, TNF receptor, Flt, Apo-1, p55, WSL-1, DR3, TRAMP, Apo-3, AIR, LARD, NGRF, DR4, DRS, KILLER, TRAIL-R2, TRICK2, and DR6; and Caspase (ICE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (containing 5% Squalene, 0.5% Tween 80, and 0.5% Span 85 (optionally containing various amounts of MTP-PE) formulated into submicron particles using a microfluidizer such as Model1 IOY microfluidizer (Microfluidics, Newton, MA)), and SAF (containing 10% Squalene, 0.4% Tween 80, 5% pluronic-blocked polymer L121, and thr-MDP, either microfluidized into a submicron emulsion or vortexed to generate a larger particle size emulsion); aluminum salts (alum), such as aluminum hydroxide, aluminum phosphate, aluminum sulfate; Amphigen; Avridine; L121/squalene; D-lactide-poly-lactide/glycoside; pluronic polyols; killed *Bordetella*; *saponins*, such as Stimulon™ QS-21 (Antigenics, Framingham, MA), ISCOMATRIX (CSL Limited, Parkville, Australia), and immunostimulating complexes (ISCOMS); *Mycobacterium tuberculosis*; bacterial lipopolysaccharides; synthetic polynucleotides such as oligonucleotides containing a CpG motif; IC-31 (Intercell AG, Vienna, Austria), a pertussis toxin (PT) or mutant thereof, a cholera toxin or mutant thereof; or an *E. coli* heat-labile toxin (LT) or mutant thereof, particularly LT-K63, LT-R72.

Suitable adjuvants used to enhance an immune response further include, without limitation, MPL™ (3-0-deacylated monophosphoryl lipid A, Corixa, Hamilton, MT). Also suitable for use as adjuvants are synthetic lipid A analogs or aminoalkyl glucosamine phosphate compounds (AGP), or derivatives or analogs thereof, which are available from Corixa (Hamilton, MT). One such AGP is 2-[(R)-3-Tetradecanoyloxytetradecanoylamino] ethyl 2-Deoxy-4-0-phosphono-3-0-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. Finally, the immunogenic product may be incorporated into liposomes for use in a vaccine formulation, or may be conjugated to proteins such as keyhole limpet hemocyanin (KLH) or human serum albumin (HSA) or other polymers.

Examples of preservatives include, for instance, thimerosal.

In practice, the exact amount of A2 polypeptide used may vary from subject to subject. Appropriate "effective amount" may be determined by one of ordinary skill in the art using only routine experimentation. In a typical embodiment, the method or composition comprises an amount of A2 polypeptide effective at causing a therapeutic immune response in the treated mammal, particularly effective at causing a therapeutic benefit in the treated mammal, such as effective at reducing or delaying symptoms of the disease, or accelerating clearance, or improving survival.

Typical compositions or formulations for use in the invention comprise (or are adapted to provide) a dose of between 1-2000 μg, preferably between 10 and 1000 μg of A2 polypeptide.

Particular compositions for use in the invention are liquid formulations. Particular compositions comprise:
recombinant A2 protein, particularly from 10 to 1,000,00 μg/mL, particularly from 50-200 μg/mL;
an adjuvant, preferably Saponin, more preferably from 0.05 to 1 mg/mL, more preferably from 0.125 to 0.500 mg/mL,
optionally a preservative, preferably Thimerosal, more preferably from 0.001 to 0.1 mL, even more preferably about 0.01 mL, and
a buffered saline solution (typically volume adjusted to 1.00 mL).

Immunotherapy

The invention provides novel immunotherapeutic methods for treating leishmaniasis based on the administration of a *Leishmania* A2 polypeptide. The method allows to substantially reduce, or suppress, the parasite load in infected animals. The treatment is able to enhance the cellular immune response, reduce the leishmaniasis symptoms, and increase survival. The invention thus reduces disease/parasite spread, does not select resistant parasites and has no side effect. The invention thereby reduces the risk of dogs being strong parasite reservoirs, thus contributing to disease eradication.

Particular embodiments and objects of the invention thus relate to a *Leishmania* A2 polypeptide for use in a method for treating leishmaniasis in an infected mammal, or in a method for treating a *Leishmania* infection in an infected mammal, or in a method for reducing *Leishmania* load in an infected mammal, or in a method for delaying the appearance of Leishmaniasis clinical signs in an infected mammal, or in a method for reducing leishmaniasis clinical signs in number and severity in an infected mammal, or in a method for preventing the spread of leishmaniasis from an infected mammal, or in a method for clarifying or generating partial or total clearance of *Leishmania* in an infected mammal.

The method/use of the invention generally comprises the administration, to an infected mammal, of an A2 polypeptide (or a composition comprising an A2 polypeptide), as defined above. Administration can be via different routes. Preferably, administration is by injection. Even more preferably, administration is by subcutaneous, intramuscular, intravenous, intra-arterial, or intraperitoneal injection, most preferably by subcutaneous injection.

The method may comprise a single administration, or repeated administrations, depending e.g., on the mammal and stage of disease. In a particular embodiment, only one injection is performed. In another particular embodiment, 2-5 injections are performed, such as 2 or 3 injections. When several injections are performed, they are typically separated by 5-30 days intervals, preferably by about 2 weeks interval.

Formulations will contain an effective amount of the active ingredient in a vehicle, the effective amount being readily determined by one skilled in the art. The active ingredient may typically range from about I % to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

The method can be used to treat mammals infected by any species of *Leishmania* protozoans, particularly *L. donovani*, *L. infantum*, *L. chagasi*, *L. braziliensis*, *L. tropica*, *L. major*, and/or *L. mexicana*.

In this regard, the invention is particularly suited to treat mammals with cutaneous leishmaniasis (CL) or visceral leishmaniasis (VL). It is particularly suited to treat canine visceral leishmaniasis.

Advantageously, the invention can be administered to the mammal independently from a preliminary diagnosis requirement.

In certain embodiments, an effective amount of the polypeptide or therapeutic composition is administered to the subject. "Effective amount" or "therapeutically effective amount" are used interchangeably herein, and refer to an amount of a compound, formulation, material, or composition, as described herein effective to achieve a particular biological result. Such results may include, but are not limited to the inhibition of infection as determined by any means suitable in the art.

In certain embodiments, "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Formulations will contain an effective amount of the active ingredient in a vehicle, the effective amount being readily determined by one skilled in the art. "Effective amount" is meant to indicate the quantity of a compound necessary or sufficient to realize a desired biologic effect. The active ingredient may typically range from about 1% to about 95% (w/w) of the composition, or even higher or lower if appropriate. The amount for any particular application can vary depending on such factors as the severity of the condition. The quantity to be administered depends upon factors such as the age, weight and physical condition of the animal considered for vaccination and kind of concurrent treatment, if any. The quantity also depends upon the capacity of the animal's immune system to synthesize antibodies, and the degree of protection desired. Typically, dosages used in vitro may provide useful guidance in the amounts useful for in situ administration of the composition, and animal models may be used to determine effective dosages for treatment of particular disorders. Additionally, effective dosages can be readily established by one of ordinary skill in the art through routine trials establishing dose response curves. The subject is immunized by administration of the composition thereof in one or more doses. Multiple doses may be administered as is required to maintain a state of immunity to the target. For example, the initial dose may be followed up with a booster dosage after a period of about four weeks to enhance the immunogenic response. Further booster dosages may also be administered. The composition may be administered multiple (e.g., 2, 3, 4 or 5) times at an interval of, e.g., about 1, 2, 3, 4, 5, 6 or 7, 14, or 21 days apart.

Combination Therapy

The immunotherapy of the invention may be used either alone or in combination with other treatments against leishmaniasis. In particular, the immunotherapy may be combined with vaccination. Alternatively, the immunotherapy may be combined with conventional chemotherapy. In this regard, examples of chemotherapy agents that can be effectively utilized in combination with immunotherapy of the present invention include, without limitation, analogs of inosine, formicine and analogues of nucleosides; antibacterial antibiotics: aminoglycosides, amphenicols, ansamycins, beta-lactams such as penicillin and cephalexins lincosamides, macrolides, polypeptides, tetracyclines, cycloserine, mupirocin, tuberines, diaminopyrimidines, nitrofurans, quinolones, sulfonamides, sulfones, enrofloxacin, paromomycin and other aminoglycosides, antiparasitic drugs: allopurinol, pentavalent antimonials (N-Methyl-meglumine, Na stibogluconate), amphotericin B, liposomal amphotericin B, aminosidine, pentamidine, alkylphosphocholines, metronidazole, buparvaquone, sitamaquine or 8 aminoquinoline and temporins, anti-fungal drugs such as: ketoconazole, fluconazole, itraconazole, terbinafine, and anti-cancer drugs such as the miltefosine and stimaquine.

The term "combination with" indicates that the treatments are administered in conjunction to the mammal, but not necessarily at the same time. Treatments may be formulated together and administered together. They may be formulated separately, and administered separately, either at essentially the same time, or sequentially, or alternately.

The terms "protein," "peptide" and "polypeptide" are used interchangeably herein.

The term "amino acid" includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in Dextrorotary or Levorotary stereoisomeric forms, as well as unnatural amino acids (e.g., phosphoserine, phosphothreonine, phosphotyrosine, hydroxyproline, and gamma carboxyglutamate; hippuric acid, octahydroindole 2-carboxylic acid, statine, 1,2,3,4, tetrahydroisoquinoline-3 carboxylic acid, penicillamine, ornithine, citruline, alpha methyl alanine, para benzoylphenylalanine, phenylglycine, propargylglycine, sarcosine, and tert butylglycine). The term also comprises natural and unnatural amino acids (Dextrorotary and Levorotary stereoisomers) bearing a conventional amino protecting group (e.g. acetyl or benzyloxycarbonyl), as well as natural and unnatural amino acids protected at the carboxy terminus (e.g., as a (C1-C6)alkyl, phenyl or benzyl ester or amide; or as an a-methylbenzyl amide). Other suitable amino and carboxy protecting groups are known to those skilled in the art. An amino acid can be linked to the remainder of a compound through the carboxy terminus, the amino terminus, or through any other convenient point of attachment, such as, for example, through the sulfur of cysteine.

The invention encompasses isolated or substantially purified protein compositions. In the context of the present invention, an "isolated" or "purified" polypeptide is a polypeptide that exists apart from its native environment and is therefore not a product of nature. A polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals. Fragments and variants of the disclosed proteins or partial length proteins encoded thereby are also encompassed by the present invention. By "fragment" or "portion" is meant a full length or less than full length of the amino acid sequence of, a polypeptide or protein.

A "variant" of a molecule is a sequence that is substantially similar to the sequence of the native molecule.

"Isolated" means altered or removed from the natural state. For example, a nucleic acid or a peptide naturally present in a living animal is not "isolated." but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

An "immune response" refers to a humoral immune response and/or cellular immune response leading to the activation or proliferation of B- and/or T-lymphocytes and/ or and antigen presenting cells. In some instances, however, the immune responses may be of low intensity and become detectable only when using at least one substance in accordance with the invention.

"Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells (CTL) can be measured, e.g., using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

Further aspects and advantages of the invention shall be disclosed in the following experimental section.

EXAMPLE

Better tools are necessary to eliminate visceral leishmaniasis (VL). Modeling studies for regional *Leishmania* elimination indicate that an effective vaccine is a critical tool. Dogs are the reservoir host of *L. infantum* in Brazil and the Mediterranean basin, and therefore are an important target for public health interventions as well as a relevant disease model for human VL. No vaccine has been efficacious as an immunotherapy to prevent progression of already diagnostically positive individuals to symptomatic leishmaniasis. We performed a double-blinded, block-randomized, placebo-controlled, vaccine immunotherapy trial testing the efficacy of a recombinant *Leishmania* A2 protein, saponin-adjuvanted, vaccine, LeishTec®, in owned hunting dogs infected with *L. infantum*. The primary outcome was reduction of clinical progression, with reduction of mortality as a secondary outcome. Vaccination as an immunotherapy reduced the risk of progression to clinically overt leishmaniasis by 25% in asymptomatic dogs (RR: 1.33 95% C.I. 1.009-1.786 p-value: 0.0450). Receiving vaccine vs. placebo reduced all-cause mortality in younger asymptomatic dogs by 70% (RR: 3.19 95% C.I.: 1.185-8.502 p-value=0.0245). Vaccination of infected-healthy animals with an anti-*Leishmania* vaccine significantly reduced clinical progression and decreased all-cause mortality. Use of vaccination in infected-healthy dogs can be a tool for *Leishmania* control.

Introduction

Use of injection of live *Leishmania major* parasites, known as "leishmanization," has been used in cutaneous leishmaniasis endemic areas to prevent future disfiguring disease. There is no in vivo evidence for use of vaccination to prevent progression of current visceral *Leishmania* spp. infection. Use of vaccination to treat clinical canine leishmaniosis in infected individuals has been used in veterinary settings with no prior investigation regarding the efficacy of such use. Only recently has a growing body of evidence surfaced indicating that immunotherapy can be efficacious as a treatment against progression of an infectious disease.

Visceral leishmaniasis (VL), as caused by *L. infantum* infection, is a zoonotic disease, causing clinical disease in dogs and humans. VL presents as a chronic immunomodulatory disease affecting the function of the phagocytic immune cells it infects. Dogs are a useful model to understand how immune modulation can impact *Leishmania* infection and its progression in natural infection settings. At present, there are no vaccines licensed for human use against leishmaniasis, but there are three veterinary vaccines in clinical use. Epidemiologic studies that modeled control of *Leishmania* transmission have shown that successful canine vaccination would greatly diminish transmission and mortality in both dogs and people.

Current manufacturers' recommendations for these veterinary vaccines are to vaccinate only seronegative animals. Although there are some interesting potential candidate vaccines against VL, there are no blinded clinical trials which evaluate the efficacy of anti-*Leishmania* vaccination as an immunotherapy in reducing clinical progression of asymptomatic-infected dogs or humans. There have been two studies evaluating vaccine as immunotherapy, the first using Leishmune in five dogs experimentally infected with *L. donovani* and 21 dogs naturally infected with *L. infantum*, or in a second study where 16 dogs infected with *L. infantum* given an experimental *L. braziliensis* subunit vaccine were followed for several months. These were small studies with no, or un-matched, non-blinded, interventions, but provide proof-of-concept that immunotherapy after vaccination is possible. Use of vaccines as immunotherapy is of veterinary importance as approximately 20% of infected dogs likely to be vaccinated are asymptomatic and seronegative.

Although most canine and human VL occurs in tropical and sub-tropical climates via vectorborne transmission, there is a surprisingly large prevalence of canine VL among hunting hounds in the U.S. The primary route of transmission in these U.S. dogs is vertical, from dam to pup. This route of transmission occurs globally. The predominant exposure of these animals to *Leishmania* occurs prior to, or possibly at the time of, birth. In settings of vertical transmission of *L. infantum*, a combination of immune control, low parasite burden, and imperfect diagnostics prevents early detection of infection in animals born to an infected mother. Dogs may not become diagnostically positive for *L. infantum* infection after vertical transmission for years after birth. In this setting, vaccination prior to exposure is not possible. Instead, vaccination as immunotherapy is best means to prevent progression to clinical disease.

Ex vivo studies, using splenic biopsy or whole blood from Indian VL patients, identified that patients infected with *L. donovani* had a T regulatory response, predominated by CD4+ T cells producing both IFN-y and predominantly IL-10. This response also occurred in dogs infected with *L. infantum* progressing to clinical VL. Ex vivo immunomodulation, using antibodies to block IL-I 0, had limited effectiveness in improving the T cell response. Other means of ex vivo immunomodulation including use of checkpoint inhibitors, particularly anti-programmed death, in both canine and human patient cells was thought to have therapeutic potential. Treatment of canine immune cells with vaccine antigens containing toll-like receptor agonists was shown by our group to recover *Leishmania* antigen-specific T cell responses and robust T helper 1-type immunity. Population-based canine anti-*Leishmania* vaccination has been shown to significantly decrease transmission to people in statistical and mathematical modeling studies. We hypothesized that immunotherapy/vaccination of *L. infantum*-infected/exposed non-clinical animals with LeishTec® will decrease progression of clinical disease.

This block-randomized, double-blinded, placebo-controlled, immunotherapy trial demonstrates the efficacy of a recombinant *Leishmania* A2 protein, saponin-adjuvanted, vaccine, LeishTec®, to prevent progression of *Leishmania* infection, and significantly decrease all-cause mortality in the most relevant animal model for leishmaniasis: the dog. This research provides critical evidence to aid efforts in developing tools, including effective vaccines, to work towards *Leishmania* elimination within the United States and globally.

Materials and Methods

Vaccine Protocol, Study Design and Participants

We performed a double-blind, block-randomized, placebo-controlled trial in owned hunting dogs from the United States. All dogs were enrolled with signed informed consent and followed the protocol approved by the University of Iowa Institutional Animal Care and Use Committee (IACUC) an AAALAC accredited institution.

LeishTec®, a recombinant A2-targeted, Quil A adjuvanted vaccine (Lot 042/15, Ceva Animal Health, Brazil) was imported into the US from Brazil (permit no: VB-150792BRA). Permission was obtained from the state veterinarian from each participating state for the clinical team to provide this experimental vaccine to animals within their state's borders. 650 hounds from across the continental U.S. were assessed for enrollment into the trial. Physical exam was performed and blood collected to evaluate inclusion criteria. Dogs younger than six months of age, pregnant, or not current for their routine deworming, rabies virus, or core respiratory disease vaccinations were excluded. Blood samples were analyzed for seropositivity to *Borrelia burgdorferi*, *Ehrlichia* spp., *Anaplasma* spp. and antigen detection of *Dirofilaria immitis* via the SNAP® 4Dx® Plus Test with confirmatory ELISA and/or qPCR. Dual-Path Platform® (DPP) Canine Visceral Leishmaniasis (CVL) test with detection via Chembios DPP® Micro Reader was employed to detect *L. infantum* seropositive samples and qPCR for *L. infantum* rDNA was used to detect *Leishmania* parasite burden. Dogs that had clinically apparent infection with *Borrelia burgdorferi*, *Ehrlichia* spp., *Anaplasma* spp., *D. immitis* or *L. infantum*, confirmed diagnostically positive for infection, were excluded from the study.

Randomization

Based on physical exam and diagnostic testing performed at enrollment, dogs were stratified into two groups: asymptomatic and negative. Dogs were classified as asymptomatic if they had either a positive DPP or qPCR leishmaniasis diagnostic test result and had less than two physical signs of infection at enrollment. Dogs were classified as negative if DPP and qPCR were negative. Equal (1:1) randomization to vaccine or placebo groups was performed using SAS 9.4 (SAS Institute, Cary, NC). Asymptomatic and negative groups were randomized separately with dogs allocated to either vaccine or placebo via block randomization to ensure that there was an equal distribution of age, sex, region, and clinical status in treatment (vaccine and placebo) groups. After block randomization, blinded treatment groups were coded by color and evaluated for overall distribution for age, sex, and geographic location. There was even distribution of these key variables in the two groups.

Owners, veterinarians, laboratory technicians, and data analysts were all blinded to treatment. All veterinarians performing physical exams and research team members performing diagnostics or statistical analyses were blinded and restricted from viewing any patient identifiers to maintain good clinical practice and reduce bias. Vaccine and samples were kept at 4° C. while in the field. Upon arrival at the laboratory samples were immediately processed and stored at –20° C. (sera) or –80° C. (whole blood). All blood and serum samples were obtained and stored with unique barcode identifiers.

Procedures

Intervention

The vaccination period for the trial began in February of 2016. Dogs received either three I mL subcutaneous injections in the left flank of either LeishTec® vaccine or sterile water, the vaccine eluent. Dogs were vaccinated three times at fourteen-day intervals with a 22 gauge, 1", needle (Day 0, 14, and 28, FIG. 1). Venous whole blood and serum samples were taken at each time point, and a physical exam was performed. Dogs were monitored for 60 minutes after administration of each dose to monitor for severe, immediate, adverse events. Caretakers were contacted within 48 hours to record any adverse events that occurred within that time. To assess the therapeutic efficacy of vaccination/immunotherapy, dogs were followed for nine months with whole blood and serum samples collected and a physical exam performed at three-month intervals (M3, M6, and M9). DPP and qPCR were performed at each time point to monitor infection status and progression of infection as indicated by parasite burden.

Parasite DNA Isolation and qPCR

QIAamp DNA Blood Mini Kit (QIAGEN, Valencia, CA) was used for DNA isolation per manufacturer's specifications for 200 μl blood. Quality and quantity of isolated DNA was assessed using a NanoDrop 2000 (Thermo Scientific, Waltham, MA). Isolated DNA (neat and 10-fold dilution) was analyzed in duplicate via qPCR in a 96-well plate format via Super Mastermix with ROX (Quanta Biosciences, Gaithersburg, MD). Each qPCR plate contained negative control nuclease-free water and samples of whole blood-extracted DNA from negative dogs. Positive control samples of 106 *Leishmania* parasites spiked into healthy canine blood and subsequent DNA extraction were tested at full-strength, 1:10, and 1:20 dilutions for each plate. Briefly, ribosomal primer sequences: Forwad 5'-AAGTGCTTTCC-CATCGCAACT (SEQ ID NO:7), Reverse 5' CGCACTAAACCCCTCCAA (SEQ ID NO:8) (Invitrogen, Life Technologies, Grand Island, NY), probe: 5' 6FAM-CGGTTCGGTGTGTGGCGCC-MGBNFQ (SEQ ID NO:9)

(Applied Biosystems, Life Technologies, Grand Island, NY) were used. Sensitivity and Specificity of qPCR as compared to clinical status and DPP as performed by this lab has been shown to be highly concordant and greater than 98%). Primers and probe were used at a concentration of 1 OnM. The assay was performed on an ABI 7000 system machine. Thermocycle profile: 95° C. for 2 min, 95° C. for 1 min, and 50 cycles of 95° C. for 15 seconds, 60° C. for 1 min. qPCR results were analyzed using ABI 7000 System SDS Software (Applied Biosystems, Life Technologies, Grand Island, NY).

Dual Path Platform® Canine Visceral Leishmaniasis (DPP® CVL) Assay

DPP® CVL test detects *Leishmania*-specific antibodies using a recombinant *Leishmania* rK28, and colloidal gold particles coupled to protein A After addition of the last buffer, the cassette test window was monitored for the appearance of a positive test line next to the control line. Test result was visually read and time to positive recorded. A single positive control line was confirmed at 4 minutes or less. All positive or questionable samples were confirmed using the Chembios microreader system which reports an intensity value and result (negative or positive).

Physical Examination

All physical exams were completed by a veterinarian at each time point. Caretakers provided information on recent travel and hunting activities and any other notable change in the dog's overall health since last visit. If a dog died between visits, information regarding observed clinical signs prior to death was provided by the caretaker. Clinical signs of leishmaniasis for staging included: lymphadenopathy, spleno- and hepatomegaly, epistaxis, alopecia, characteristic macular or papular skin lesions, poor hair coat, cachexia as measured by low body condition score compared to rest of group, conjunctivitis, and onchogryphosis.

Outcomes

As the focus of this study was to investigate how vaccination might alter the course of disease in already infected animals, the primary outcome for this trial was to identify whether there was a difference in clinical disease progression from Day 0 and Month 9 between vaccine and placebo groups. All analyses of trial data compared time 0 to month 9 outcomes for all dogs. Clinical progression was defined by a composite clinical score comprised of the two diagnostic results (positive result for either equaled one point) and signs of leishmaniasis identified during physical exam (presence of a clinical sign added one point each). A reduction in composite clinical score between Day 0 and Month 9 indicated improvement in a dog's *Leishmania* status. An increase in composite clinical score in dogs with diagnostic evidence of infection indicated progression of leishmaniasis.

As leishmaniasis in both canine and human patients is an immunosuppressive disease that is fatal if untreated, all-cause and leishmaniasis-related mortality were evaluated as secondary outcomes. All-cause mortality was defined as mortality for any reason including leishmaniasis. Boarded veterinarians established leishmaniasis-related deaths by previous *Leishmania*-specific diagnostic results, history, and clinical signs as well as immediate cause of death (renal failure, etc.).

Statistical Analysis

Sample size was calculated based on estimation that 20% of enrolled dogs would be asymptomatic for leishmaniasis upon enrollment based on a decade of observation of this population. We expected to observe an additional 10% of dogs identified as negative at the beginning of the trial to become diagnostically positive within the time of the trial. The total *L. infantum* infected group for final analyses was defined as all animals diagnostically positive at enrollment plus all dogs that became diagnostically positive during the time of the trial. Due to husbandry practices of this group we estimated that we would have a loss of 15% of dogs throughout the trial due to reasons other than death. To observe a significant benefit in vaccination/immunotherapy, we expected to see a 25% decrease in clinical progression to symptomatic status from the vaccine. Previous observation of this cohort has shown that 50% of dogs asymptomatic for disease progress to symptomatic disease within a year. Based on this information, a sample size of 46 asymptomatic dogs per treatment would be needed to provide 80% power at an alpha of 0.05.

We have previously observed that dogs can progress to clinical disease rapidly over a three-month period, leading to large changes in composite clinical score in that time. To control for these changes, a per-protocol analysis was used determined as receiving at least one round of vaccination/placebo of the series and complete data for Day 0 and Month 9 or clinical data as described upon death. One-sided, chi-squared or Fisher's Exact test was used to determine relative risk ratios for primary and secondary outcomes while difference between continuous demographic variables was determined via t-tests using SAS 9.4 (SAS Institute, Cary, NC) and/or GraphPad Prism 7 (La Jolla, CA).

Results

Demographics

Between December 2015 and February 2016, 650 hunting dogs were assessed for study eligibility. Of 650 dogs, 72 were excluded as they were not available for follow-up. Twenty-one dogs were excluded due to failure to meet inclusion criteria (pregnant or symptomatic for leishmaniasis, Lyme disease, Ehrlichiosis, or Anaplasmosis). Five hundred fifty-seven dogs were randomized to receive either vaccine or placebo. Five hundred forty-six dogs received the first round of vaccination/placebo at Day 0 (274 vaccine, 272 placebo). Over 9 months of study, 24 dogs from vaccine group and 31 dogs from placebo group were lost to follow up. There were no statistically significant differences in age, sex, or region from which dogs were lost throughout the study indicating loss was random. Age, sex, region, and other vector-borne disease seropositivity were equally distributed between vaccine and placebo groups at enrollment. There was equal distribution between dogs with a clinical status of asymptomatic at enrollment between the two groups.

The final demographics had an equal distribution of males and females in each group. There were no statistically significant differences in regional distribution between groups (Table 1).

TABLE 1

Demographics for per-protocol. Information on age sex and region for all dogs in the per-protocol analysis.

| Variable | Immunotherapy (n = 252) | Placebo (n = 242) |
|---|---|---|
| Age, mean ± SD | 4.11, 2.45 | 3.95, 2.29 |
| Sex, % male | 47.22 | 50.00 |
| Region, % | | |
| Mid-West | 21.43 | 19.42 |
| South | 18.25 | 12.81 |

TABLE 1-continued

Demographics for per-protocol. Information on age sex and region for all dogs in the per-protocol analysis.

| Variable | Immunotherapy (n = 252) | Placebo (n = 242) |
|---|---|---|
| East | 48.02 | 53.72 |
| West | 12.30 | 14.05 |

The average age of death during the study was 6.16 years in the vaccine group and 6.14 years in the placebo group. There was no statistically significant difference in mortality rates based on sex between vaccine and placebo groups; fewer males died in both groups (47% vaccine, 37% placebo).

Research has shown that immune senescence leads to an inability to respond to vaccination in older people. Hunting hounds older than 6 years were less able to maintain asymptomatic *Leishmania* infection. To control for immune senescence, data was stratified as 6 years of age and younger vs. older than 6 years of age for all outcomes.

Clinical Progression

The population of asymptomatic animals that received vaccine/immunotherapy had a statistically significant decrease in clinical score over the nine months of trial, indicating decreased progression of disease (Table 2).

Fisher's Exact test for significance. Clinical status unadjusted relative risk determined as relative risk between symptomatic and not symptomatic based on treatment group (vaccine vs. placebo).

This effect was significant regardless of age. To address the potential effects of age, sex, region and tick-borne infection serological status on the outcome of vaccine efficacy as measured by clinical progression, we performed a multivariate logistic regression analysis to assess the relative risk of clinical progression, controlling for these other important biological variables. Asymptomatic dogs that received placebo treatment were 1.33× more likely to have an increased clinical score after nine months of follow-up indicating increased clinical progression above that seen in asymptomatic dogs that received vaccine (RR: 1.33 95% C.I. 1.009-1.786 p-value: 0.0450), (Table 3).

TABLE 2

| Variable | Vaccine (n = 57) | Placebo (n = 57) | Unadjusted relative risk | p-value |
|---|---|---|---|---|
| Age*, mean ± SD (range) | 4.25, 2.36 (0.5, 10) | 3.73, 2.31 (0.5, 9) | N/A | 0.86 |
| Sex, % male | 47.37 | 59.65 | 1.26 | 0.19 |
| Region, % | | | N/A | 0.47 |
| Mid-West | 43.86 | 35.09 | | |
| South | 10.53 | 7.02 | | |
| East | 42.11 | 49.12 | | |
| West | 3.51 | 8.77 | | |
| Clinical status, % | | | | |
| Negative | 5.26 | 8.77 | 1.13 | 0.34 |
| Asymptomatic | 66.67 | 59.65 | | |
| Symptomatic | 28.07 (n = 16) | 31.58 (n = 18) | | |
| Mean clinical score change ± SD | 0.65, 1.80 | 1.02, 1.43 | N/A | 0.04 |
| Mortality <6 years old | | | | |
| All-cause, % | 6.52 (n = 3) | 20.41 (n = 10) | 3.13 | 0.03 |
| Leish-related % | 4.44 (n = 2) | 11.36 (n = 5) | 2.56 | 0.11 |
| Vector borne disease positive (%) | | | | |
| *Borrelia burgdorferi* | 33.33 (n = 18) | 33.93 (n = 19) | N/A | 0.53 |
| *Dirofilaria immitis* | 3.70 (n = 2) | 1.79 (n = 1) | | |
| *Anaplasma* spp. | 14.81 (n = 8) | 25.00 (n = 14) | | |
| *Ehrlichia* spp. | 31.48 (n = 17) | 25.00 (n = 14) | | |

*Data may be incomplete due to missing information.

Table 2 provides demographic information for dogs included in final analysis. 114 dogs exposed to *Leishmania* included in the final analysis, includes dogs with full data from Dy 0 through Month 9 and dogs that died during the trial. Clinical status as determined by qPCR, DPP® CVL, and physical exam (composite clinical score), age, region, mortality, mean clinical score change (Month 9-Day 0), and vector-borne disease seropositivity as determined by the SNAP® 4D® Plus Test and confirmed by ELISA. Age differences between vaccine and placebo group assessed via two-sided unpaired t-test. Mean clinical score change assessed via one-sided Mann-Whitney test. Region and vector borne disease seropositivity assessed via Pearson's chi-squared test for significance. Clinical status and mortality assessed via one-sided Pearson's chi-squared test and

TABLE 3

Relative risk ratios for primary outcomes. When adjusted for age, sex, geographic location, vaccine prevents progression and death in L. infant-infected dogs.

| Outcome | Relative Risk (Placebo/Immunotherapy) | 95% C.I. | P-Value |
|---|---|---|---|
| Disease Progression of Infected | | | |
| Asymptomatic Dogs | 1.33 | 1.009-1.786 | 0.045 |
| ≤6 years old* | 1.42 | 1.032-4.309 | 0.041 |
| >6 years old | 0.78 | 0.419-1.296 | 0.205 |

TABLE 3-continued

Relative risk ratios for primary outcomes. When adjusted for age, sex, geographic location, vaccine prevents progression and death in L. infant-infected dogs.

| Outcome | Relative Risk (Placebo/ Immunotherapy) | 95% C.I. | P-Value |
|---|---|---|---|
| Mortality-Infected Asymptomatic Dogs ≤ 6 years old | | | |
| All Cause* | 3.129 | 1.185-8.502 | 0.0245 |
| Leishmaniasis-Related | 2.557 | 0.7418-8.981 | 0.1127 |

The results in bold are those that are statistically significant.
*Indicates statistically significant difference of placebo group from vaccinated group at p < 0.05.

In a separate model that addressed age of dogs in two different groups, dogs less than 6 years of age that received placebo treatment were 1.4× more likely to have an increased clinical score (RR: 1.418 95% C.I.: 1.019-2.02 p-value: 0.0409). This protective effect of vaccination against clinical progression of leishmaniosis was not seen in dogs older than six that received placebo (RR: 1.28 95% C.I.: 0.7719-2.383 p-value: 0.2051). This lack of significant benefit of vaccine in older populations is likely to have occurred for two disparate reasons: this population was small (17 dogs asymptomatic for leishmaniasis were <6 at enrollment), so it limited the ability to detect significant changes and immune senescence likely decreased the benefit from immunotherapy.

Mortality

Figure 2:
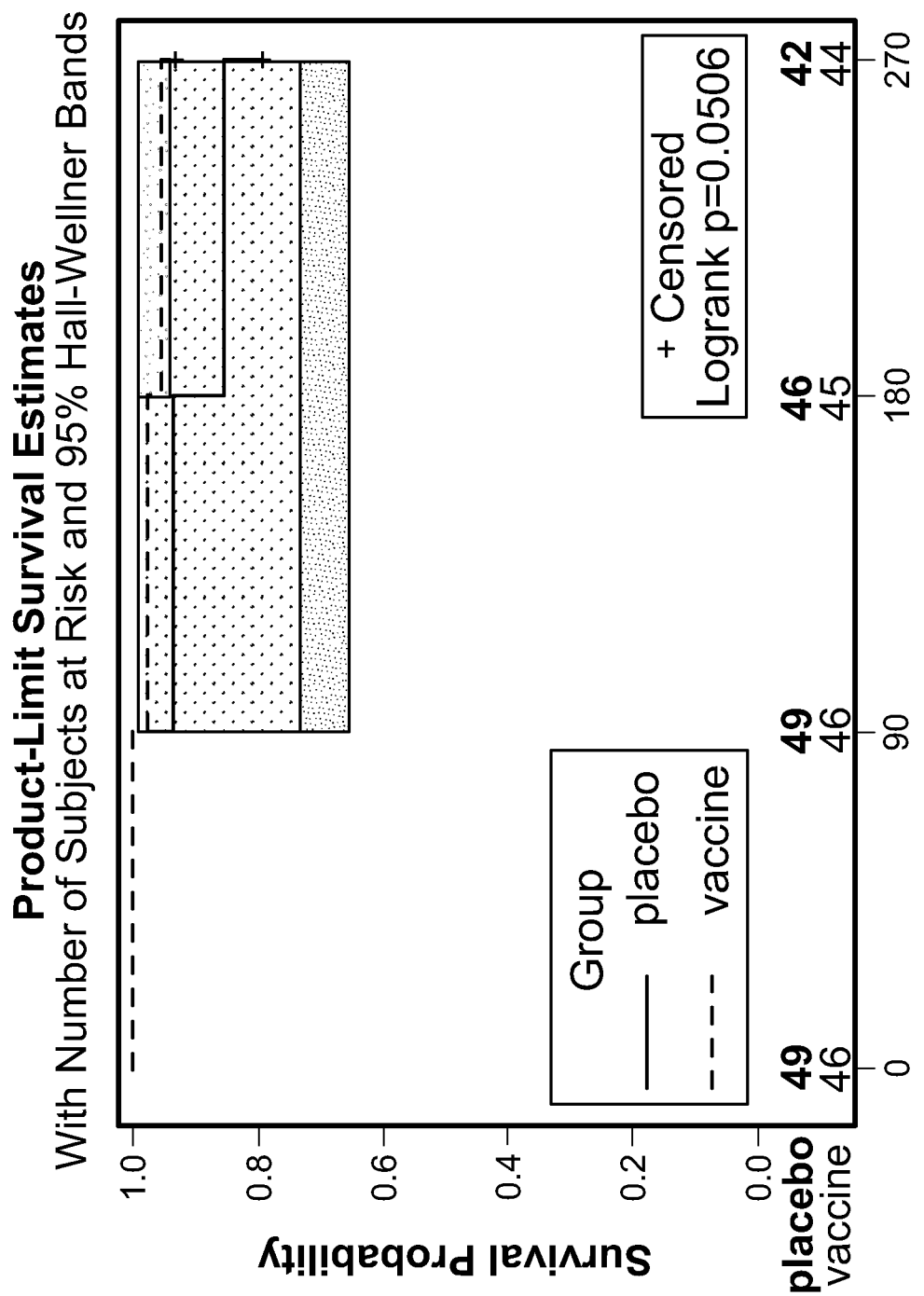
FIG. 2. Performance of vaccine to prevent all-cause mortality and decrease leishmaniasis-related mortality in asymptomatic, *L. infantum*-infected dogs. All-cause mortality. Product-Limit survival estimates. Placebo—black line, vaccine gray line. 95% Hall-Wellner bands depicted via shading. Chi-square: 3.8 p-value=0.05. n=41 total, 19 vaccine, 22 placebo.

Leishmaniasis can alter the overall health and increase likelihood of death in an infected individual due to *L. infantum* intracellular infection of macrophages and concomitant immune alterations. With the goal of providing aid to dogs once already infected, we were interested in understanding of how vaccination as an immunotherapy may alter all-cause mortality in *Leishmania*-infected populations. There was a statistically significant increase in risk of all-cause mortality in asymptomatic dogs that received placebo vs. vaccine (RR: 3.19 95% C.I.: 1.185-8.502 p-value=0.0245, FIG. 2) for animals less than or equal to 6 years of age.

Figure 3:
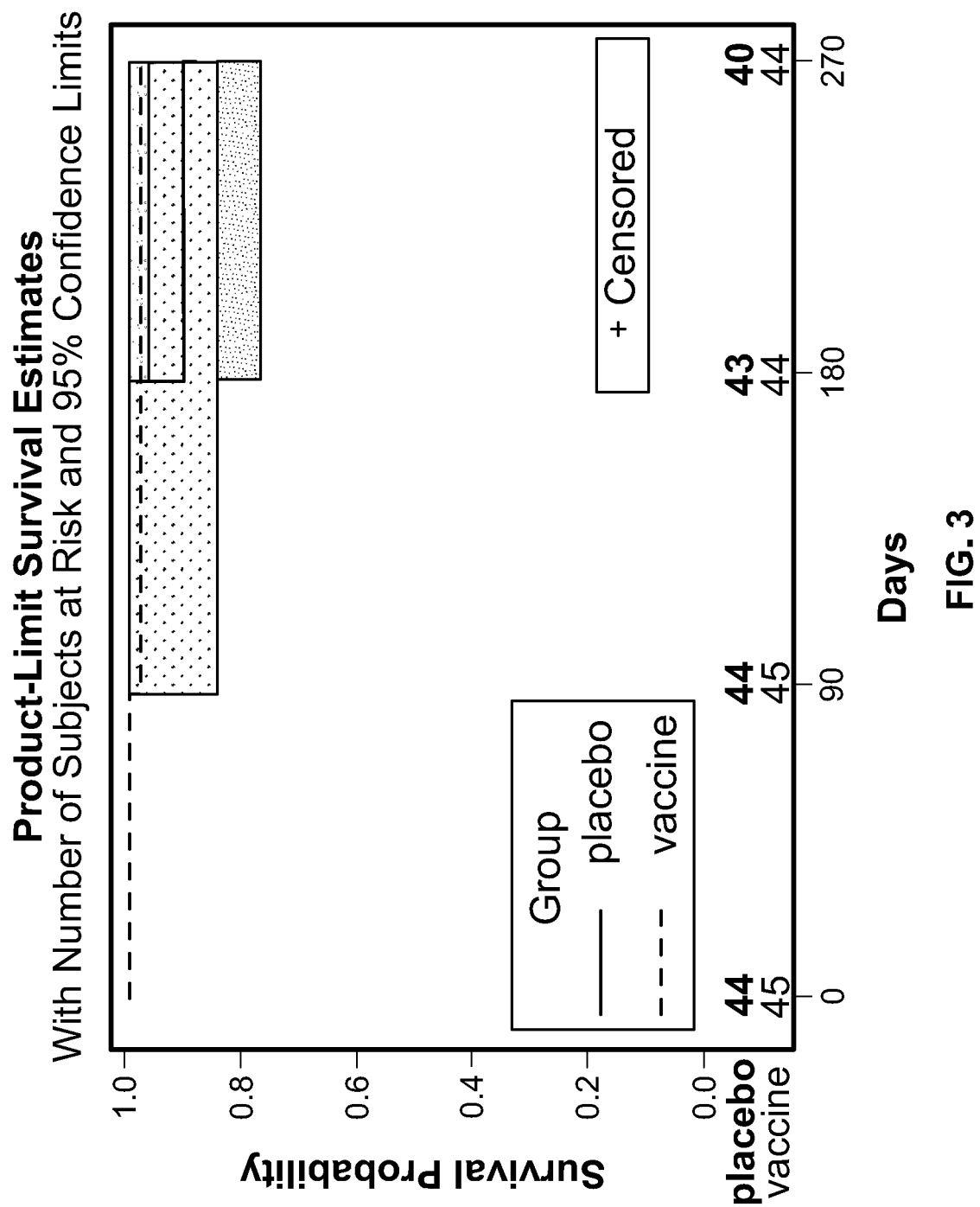
FIG. 3. All-cause mortality. Product-Limit survival estimates. Placebo—black line, vaccine gray line. 95% Hall-Wellner bands depicted via shading. Chi-square: 3.8 p-value=0.05. n=41 total, 19 vaccine, 22 placebo.

The risk of *Leishmania*-related death was also increased in populations receiving placebo as compared to vaccine (RR: 2.557 95% C.I.: 0.7418-8.981 p-value=0.1127, FIG. 3).

Figure 4A:
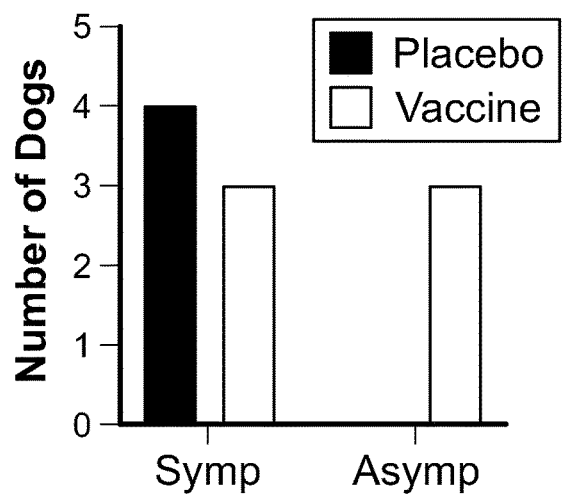
FIGS. 4A-4C. Impact of vaccine on animals that became symptomatic during month of vaccination series.
Figure 4B:
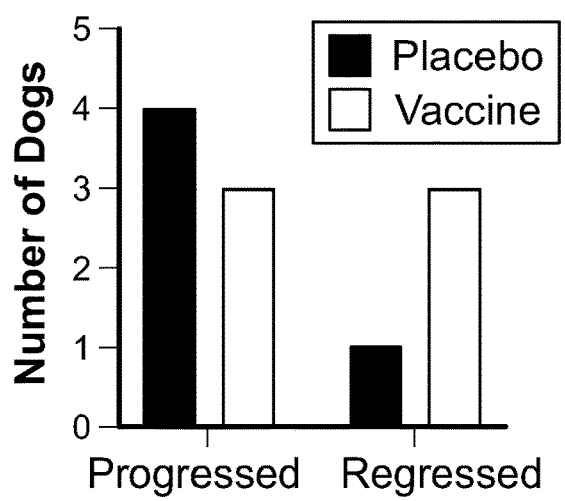
Figure 4C:
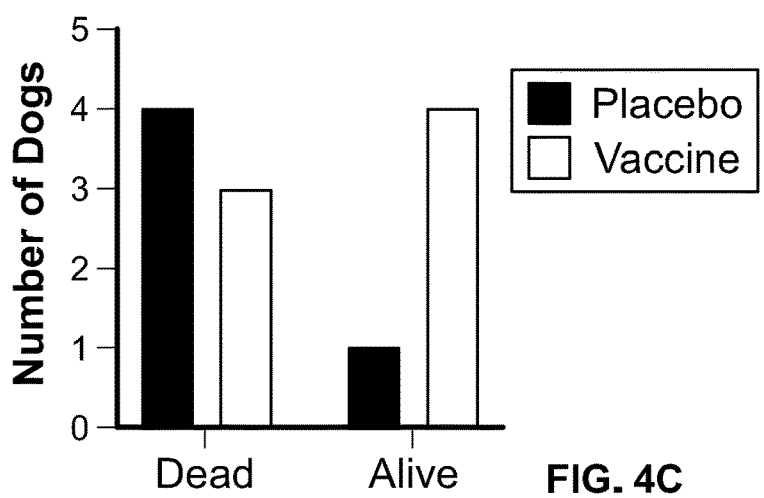

It is of great clinical interest whether vaccine immunotherapy could alter the course of disease once a dog was symptomatic. In this trial, however, we did not enroll symptomatic animals. Ten dogs became symptomatic within the time of receiving the series of vaccine. We evaluated dogs that became symptomatic during the first month of the trial, during the vaccination phase, to explore whether there was a benefit to receiving vaccine immunotherapy after symptoms appeared (FIGS. 4A-4C). There was an increased risk of maintaining symptomatic status at month 9 for dogs that received placebo vs. vaccine (RR: 2.0, 90% C.I. 1.027-2.284, p-value 0.1667). Despite a lack of statistical significance in these findings due to a small sample size, a trend of benefit from immunotherapy in symptomatic dogs was observed.

A secondary analysis was performed to evaluate whether vaccine as immunotherapy would alter parasite burden as measured by qPCR. We evaluated qPCR as a binomial variable (Y/N) for each dog at time 0 and month 9 and compared whether there was a change in the number of dogs qPCR positive at the end of 9 months compared to time 0. There was no significant difference found between vaccinated and placebo groups for qPCR positivity, indicating that although vaccine as immunotherapy did alter serological outcomes and physical status, it did not induce a reduction in the number of animals with detectable parasitemia.

Vaccine Safety

Safety was assessed after each vaccination and reviewed by a volunteer data safety monitoring board. There was an overall adverse event rate of 1.86% within the population with a 3.09% adverse event rate in vaccinated animals. The majority of adverse events reported were mild swelling or soreness at the site of injection. There was no statistically significant relationship between the occurrence of adverse events and infection status. This suggests this vaccine was not only efficacious but also safe for use in infected, non-clinical, animals.

Discussion

New tools are needed to control Leishmaniasis globally. The possibility that vaccination could both alter the course of VL for an individual and aid in elimination of disease in populations is an alluring prospect. As a first step towards establishing whether vaccination of dogs in endemic areas could help reduce the reservoir source for continued sand fly or vertical transmission, this trial demonstrates that vaccination of asymptomatic dogs decreased both progression and mortality over a 9 month period. Vaccination as immunotherapy reduced the risk of progression to clinically overt leishmaniasis by 25% in all asymptomatic dogs regardless of age and by 30% in asymptomatic dogs 6 years of age or younger. Receiving vaccine vs. placebo reduced all-cause mortality in asymptomatic dogs 6 years of age or younger by 70%. A similar trend was seen in protection against death due to leishmaniosis, but there were not enough deaths due to leishmaniosis overall to achieve statistical power for this comparison.

Current guidelines for all three licensed canine *Leishmania* vaccines prohibit vaccination of seropositive animals. In Brazil, despite many improvements for both human and canine patients, seropositive dogs still must be reported to the Ministry of Health to be culled. Miltefosine was recently approved for treatment of dogs. Although treatment of dogs believed to have leishmaniosis in Brazil is now possible, public health regulations to protect human health by culling seropositive animals have not been amended. Even when treatment of leishmaniosis is not made more difficult by federal law, chemotherapies used to treat leishmaniasis have high rates of adverse reaction to treatment. This study highlights potential use of vaccination in infected healthy animals as immunotherapy. Further study focused on use of LeishTec® in symptomatic animals would be required to achieve statistically significant findings and a recommendation for its use in symptomatic animals.

Because of the high-risk, sporting, lifestyle of the dogs in this trial, there was a larger number of animals lost to follow up. Similar or greater loss has been seen in other field trials for canine leishmaniosis vaccines. This loss was not statistically different between interventions, but did decrease the power of study observations and diminished our ability to find statistically significant sub-analyses. This population of dogs is transient by nature with kennels trading animals between geographic locations and animals retiring from active hunting and residing away from the study kennel. Despite this, we observed statistically significant changes due to immunotherapy, highlighting the impact of this study on current and future interventions. We utilized clinically relevant, standard-of-veterinary care, diagnostic technologies in this trial. Due to immune alterations that occur during infection with *L. infantum*; an obligate intracellular, immunocompromising parasitic infection, and the less than 100% perfect nature of any diagnostic test, there is likely to be a small percentage of healthy infected dogs that remained diagnostically negative over the course of the trial. Based on this, there is an inherent misclassification bias present. Although the results of this trial may have significant implications, it was performed in a non-endemic area for leishmaniasis using dogs that had primarily, if not exclusively, received their infection while in utero via vertical transmission. The clinical and immunologic progression of these dogs has been previously shown to be very similar, if not identical, to that of animals from endemic areas. Despite this, different effects from vaccination may be observed in holoendemic regions where the pressure of sand fly transmission is greater than in this trial.

Both asymptomatic dogs and people are thought to potentially have a significant role in transmission and maintenance of *Leishmania* parasites within the population of endemic countries including Brazil, and possibly India. Xenodiagnosis studies performed in dogs of varied clinical status with qPCR data has shown that clinical status (being clinically ill vs. not) was more highly correlated with transmission of parasites from the dog to the sand fly than blood qPCR. This study provides robust data indicating that vaccination reduced clinical progression in dogs infected with *L. infantum*, indicating that vaccination may also decrease transmissibility.

Pathogen antigens are unique in both their immunogenicity and ability to elicit protective and/or pathogenic immune responses. The concept of immunotherapy of *L. infantum* infection by vaccination considers the ability of vaccine antigen(s) to overtake the immune response from an immune system already responding to a wide variety of *Leishmania* antigens and promote protective immunity. We previously published that dogs given different *Leishmania* vaccine antigens, with and without addition of Toll like receptor agonists, can prompt very different responses from CD4 and CD8 T cells. Here we show that addition of a specific recombinant protein (here A2), through vaccination, can skew the immune response towards a more protective response.

Reducing progression of disease could improve longevity of both animals and humans infected with visceralizing *Leishmania* spp. Utilizing vaccination as immunotherapy has been evaluated for the treatment of cancer and other infectious diseases. Due to evidence that indicates there are limited side effects of such immunotherapies which produce robust immune responses that control progression of disease, this therapeutic approach predominates many pharmaceutical company research and development portfolios. This study shows the ability of a licensed leishmaniasis vaccine to be used as an effective immunotherapy in reducing progression of disease and mortality in an infected asymptomatic population. This is groundwork for immunotherapy use in both humans and animals to reduce occurrence of leishmaniasis and encourages further study to identify if this type of intervention can alter disease transmission.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and "or" and similar referents in the context of describing the invention are to be construed to cover both the singular and the plural, unless otherwise indicated herein or clearly contradicted by context. Thus, for example, reference to "a subject polypeptide" includes a plurality of such polypeptides and reference to "the agent" includes reference to one or more agents and equivalents thereof known to those skilled in the art, and so forth.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention. Further, all publications mentioned herein are incorporated by reference in their entireties.

The ASCII text file "Sequence.txt" created on Sep. 22, 2021, having the size of 5 KB, is incorporated by reference into the specification.

What is claimed is:

1. A method for treating a *Leishmania*-infected dog, comprising administering to the dog an immunogenic composition comprising a recombinant *Leishmania* A2 polypeptide, as an antigen and saponin as an adjuvant, wherein the composition is administered by subcutaneous injection 1, 2 or 3 times, and wherein the dog is infected by *Leishmania infantum* and has visceral leishmaniasis (VL).

2. A method of reducing *Leishmania* load or delaying the appearance of Leishmaniasis clinical signs in a *Leishmania*-infected dog, comprising administering to the dog an immunogenic composition comprising a recombinant *Leishmania* A2 polypeptide, as an antigen and saponin as an adjuvant, wherein the composition is administered by subcutaneous injection 1, 2 or 3 times, and wherein the dog is infected by *Leishmania infantum* and has visceral leishmaniasis (VL).

3. A method of preventing the spread of leishmaniasis from a *Leishmania*-infected dog, comprising administering to the dog an immunogenic composition comprising a recombinant *Leishmania* A2 polypeptide as an antigen and saponin as an adjuvant, wherein the composition is administered by subcutaneous injection 1, 2 or 3 times, and wherein the dog is infected by *Leishmania infantum* and has visceral leishmaniasis (VL).

4. The method of claim 1, wherein the recombinant A2 polypeptide is produced in prokaryotic recombinant host.

5. The method of claim 1, wherein the A2 polypeptide is from an amastigote form of *Leishmania*.

6. The method of claim 1, wherein the A2 polypeptide comprises SEQ ID NO: 1 or 2.

7. The method of claim 1, wherein the A2 polypeptide comprises all or part of an amino acid sequence selected from SEQ ID Nos: 3-6 or of natural variants thereof.

8. The method of claim 1, wherein the composition is formulated with an excipient.

9. The method of claim 8, wherein the excipient is a saline solution.

10. The method of claim 1, wherein the composition comprises:
   (a) 50 to 200.00 μg/mL of recombinant A2 protein,
   (b) 0.125 to 0.500 mg/mL Saponin,
   (c) 0.01 mL Thimerosal, and
   (d) volume adjusted to 1.00 mL with buffered saline solution.

11. The method of claim 1, wherein the A2 polypeptide is administered in combination with chemotherapy.

12. The method of claim 1, wherein the A2 polypeptide comprises two repeats of SEQ ID NO: 1 or 2.

* * * * *

UNITED STATES PATENT AND TRADEMARK OFFICE
CERTIFICATE OF CORRECTION

| | |
|---|---|
| PATENT NO. | : 11,833,197 B2 |
| APPLICATION NO. | : 16/969889 |
| DATED | : December 5, 2023 |
| INVENTOR(S) | : Christine Petersen and Angela Toepp |

It is certified that error appears in the above-identified patent and that said Letters Patent is hereby corrected as shown below:

In the Specification

Column 20,
Line 60, "of 106" should read --$10^6$--.

Signed and Sealed this
Sixteenth Day of July, 2024

Katherine Kelly Vidal
*Director of the United States Patent and Trademark Office*